United States Patent [19]

Ocain et al.

[11] Patent Number: 5,739,169

[45] Date of Patent: Apr. 14, 1998

[54] AROMATIC COMPOUNDS FOR INHIBITING IMMUNE RESPONSE

[75] Inventors: Timothy D. Ocain, Framingham; Huai Gao, Groton; Jeffrey L Krieger, Newton; Theresa M. Sampo, Boston, all of Mass.

[73] Assignee: Procept, Incorporated, Cambridge, Mass.

[21] Appl. No.: 656,468

[22] Filed: May 31, 1996

[51] Int. Cl.$^6$ .................. A61K 31/135; A01N 33/02; C07C 229/00
[52] U.S. Cl. .................. 514/658; 562/456; 562/457
[58] Field of Search .................. 562/456, 457; 514/658

[56] References Cited

U.S. PATENT DOCUMENTS

| | | | |
|---|---|---|---|
| 3,313,848 | 4/1967 | Scherrer et al. | 260/518 |
| 4,089,974 | 5/1978 | Conrow et al. | 424/319 |
| 4,910,282 | 3/1990 | Abraham et al. | 528/185 |
| 5,347,038 | 9/1994 | Arndt et al. | 560/48 |

FOREIGN PATENT DOCUMENTS 59-167548  9/1984  Japan.

OTHER PUBLICATIONS

Edwards, R. L. and Kale, N., "The Synthesis of Aurantiacin," *J. Chem. Soc.*, 4084–4085 (1964).

Wassmundt, F. W. and Kiesman, W. F., "Efficient Catalysis of Hydrodediazoniations in Dimethylformamide," *J. Org. Chem.*, 60: 1713–1719 (1995).

Scherrer, R. A. and Beatty, H. R., "Preparation of Ortho--Substituted Benzoic Acids by the Copper (II)—Catalyzed Reaction of Diphenyliodonium-2-Carboxylate with Anilines and Other Nucleophiles," *J. Org. Chem.*, 45: 2127–2131 (1980).

Pentikäjnen, P. J., et al., "Human Pharmacokinetics of Tolfenamic Acid, a New Anti–Inflammatory Agent," *Eur. J. Clin. Pharmacol.*, 19:359–365 (1981).

Zabrowski, D. L., et al., "The Oxidation of Aromatic Amines in the Presence of 'Electron–Rich' Aromatic Systems," *Tetrahedron Letters*, 29 (36) :4501–4504 (1988).

Winder, C. V., et al., "Anti–Inflammatory, Antipyretic and Antinociceptive Properties of N–(2,3–xylyl) Anthranilic Acid (Mefenamic Acid)," *J. Pharmacol. Exp. Ther.*, 138: 405–413 (1962).

Winder, C. V., et al., "Comparative Bioassay of Drugs in Adjuvant–Induced Arthritis in Rats: Flufenamic Acid, Mefenamic Acid, and Phenylbutazone," *Arthritis and Rheumatism*, 12(5): 472–482 (1969).

Winder, C. V., et al., "Anti–Inflammatory and Antipyretic Properties of N–(α, α, α–Trifluoro–m–tolyl) anthranilic Acid (CI–440; Flufenamic Acid), " *Arthritis and Rheumatism*, 6 (1): 36–47 (1963).

*Primary Examiner*—Mukund J. Shah
*Assistant Examiner*—Bruck Kifle
*Attorney, Agent, or Firm*—Hamilton, Brook, Smith and Reynolds, P.C.

[57] ABSTRACT

Novel compounds

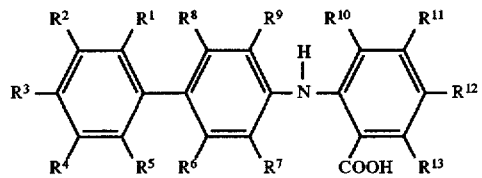

wherein $R^1$ to $R^{13}$ are independently selected from $C_2-C_4$ linear and branched alkyls, H, $NH_2$, $CH_3$, $OR^{14}$, fluorine, chlorine, iodine, $NO_2$, $CF_3$, $NHCOCH_3$, $NHCOOtBu$, $NHR^{15}$, $NR^{16}R^{17}$ and phenyl, for use as immunosuppressive agents to prevent or significantly reduce graft rejection in organ and bone marrow transplantation are described. The novel compounds can also be used as an immunosuppressant drug for T-lymphocyte mediated autoimmune diseases, such as diabetes, and may be useful in alleviating psoriasis and contact dermatitis. Additionally, the novel compounds can be used for antiproliferation and gene therapy.

5 Claims, No Drawings

AROMATIC COMPOUNDS FOR INHIBITING IMMUNE RESPONSE

BACKGROUND OF THE INVENTION

Replacement of defective or severely injured tissues and organs has been a medical objective as long as medicine has been practiced. Grafts from an individual to himself almost invariably succeed, and are especially important in the treatment of burn patients. Likewise, grafts between two genetically identical individuals almost invariably succeed. However, grafts between two genetically dissimilar individuals would not succeed without immunosuppressive drug therapies. The major reason for their failure is a T cell mediated immune response to cell-surface antigens that distinguish donor from host.

Immunosuppressive agents are also indicated in the treatment of autoimmune diseases such as rheumatoid arthritis or type I diabetes mellitus. One particular condition worth mentioning here is psoriasis. This disease is characterized by erythematous patches of skin accompanied by discomfort and itching. Hyperplasia of the epidermis involving proliferation of keratinocytes is also a hallmark feature of psoriasis. An inflammatory component is suggested by: (i) the finding of lymphocytic infiltration of epidermis, and (ii) the fact that immunosuppressive agents such as cyclosporin and corticosteroids have beneficial effect on the disease.

A number of drugs are currently being used or investigated for their immunosuppressive properties. Among these drugs, the most commonly used immunosuppressant is cyclosporin A. However, usage of cyclosporin has numerous side effects such as nephrotoxicity, hepatotoxicity and other central nervous system disorders. Thus, there is presently a need to investigate new immunosuppressive agents that are less toxic but equally as effective as those currently available.

SUMMARY OF THE INVENTION

This invention relates to novel compounds that are useful as immunosuppressive agents to prevent or significantly reduce graft rejection in organ and bone marrow transplantation. The novel compounds can also be used as an immunosuppressant drug for T lymphocyte mediated autoimmune diseases, such as diabetes, rheumatoid arthritis, multiple sclerosis, lupus erythematosus, ulcerative colitis, autoimmune uveitis and steroid resistant asthma In another aspect, other diseases with suspected inflammatory components, such as psoriasis, contact dermatitis and hyperplasia of the epidermis, can be treated with the novel compounds of this invention to alleviate symptoms associated with these disease states.

It is known that compounds having T lymphocyte immunosuppressive properties may also be useful in inhibiting the proliferation of cardiac smooth muscle cells. Based upon this, it is expected that the compounds can be used for the treatment of hyperproliferative vascular disorders, such as restenosis and atherosclerosis.

The invention also provides a method for coadministration of the compounds described herein with agents designed for gene therapy. It is believed that the use of the compounds of this invention may suppress the immune system and reduce/minimize an immune response against the gene delivery vehicle, so that therapeutic levels of transgene expression can be achieved in an animal or human.

DETAILED DESCRIPTION OF THE INVENTION

This invention is based upon the discovery that of novel compounds that can inhibit antigen specific T lymphocyte proliferation in vitro. The data suggest that these novel compounds have potential use as immunosuppressants to reduce undesirable immune responses in humans. The compounds of this invention can be used to facilitate organ transplantation, and to treat human autoimmune disorders where the specific activation of T cells is responsible for, or contributes to the pathology and progression of the diseases, such as diabetes, rheumatoid arthritis, multiple sclerosis, lupus erythematosus, ulcerative colitis, autoimmune uveitis and steroid resistant asthma.

This invention pertains to novel compounds that have immunosuppressive properties of the general formula:

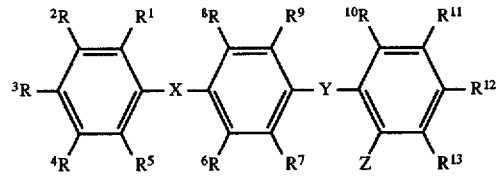

and physiologically acceptable salts thereof;

wherein X and Y are independently selected from the group consisting of 0 to 1 methylene units (i.e. $CH_2$), heteroatoms (e.g., oxygen, nitrogen, sulfur), CO, $SO_2$, $SO_2NH$ and NH;

wherein $R^1$ to $R^{13}$ are independently selected from the group consisting of (e.g., $C_2$-$C_4$, linear and branched alkyls), H, $NH_2$, $CH_3$, $OR^{14}$ (e.g. $C_2$-$C_8$ linear and branched alkyls), halogen (e.g., fluorine, chlorine, bromine, iodine), $NO_2$, $CF_3$, $NHR^{15}$, $NR^{16}R^{17}$, $NHCOCH_3$, NHCOOtBu and phenyl;

wherein $R^{15}$ is selected from the group consisting of $C_2$-$C_4$ linear and branched alkyls;

wherein $R^{16}$ and $R^{17}$ are independently selected from the group consisting of H and $C_2$-$C_4$ linear and branched alkyls;

wherein Z is selected from the group consisting of tetrazole, $CO_2R^{18}$ and $COR^{18}$;

wherein $R^{18}$ is selected from the group consisting of $C_1$-$C_5$ linear and branched alkyls, $NH_2$, H, substituted or unsubstituted aryl or heteroaryl and amino acids;

wherein one or more of the aromatic rings can be substituted with nitrogen;

wherein two of the aromatic rings can be optionally linked together by a bond selected from the group consisting of $CH_2$, oxygen, sulfur, NH and CO.

Aromatic ring substitution can be ortho, meta or para. Preferably, the aromatic ring substitution of substituents is para, in relation to attachment between two aromatic rings.

The compounds of this invention have aromatic moieties that can be fully or partially substituted with the groups defined above. Alternatively, one, two or all three of the aromatic moieties can remain unsubstituted. The preferred position of the Z substituent is ortho, however, it could be interchanged for positions designated above as $R^{10}$ to $R^{12}$.

In the preferred embodiment, the novel compounds are represented by the following general formula:

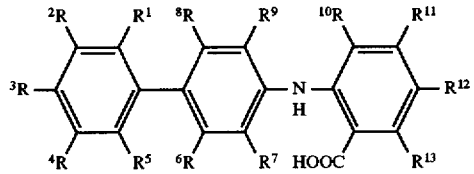

and physiologically acceptable salts thereof;

wherein $R^1$ to $R^{12}$ are defined above. Examples of specific compounds having the general formula are shown with experimental preparations detailed below.

In another embodiment, the compounds are represented by the following general formula:

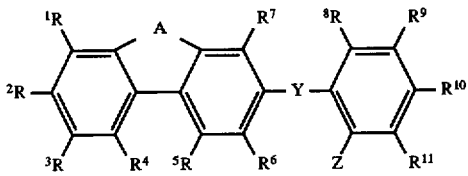

and physiologically acceptable salts thereof;
wherein $R^1$ to $R^{11}$, Z and Y are defined above; and
wherein A is selected from the group consisting of $CH_2$, oxygen, sulfur, NH and carbonyl.

In yet another embodiment, the novel compounds comprise two aromatic moieties and are represented by the general formula:

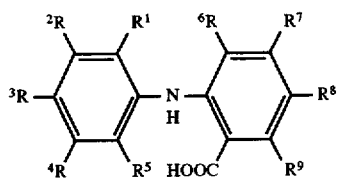

and physiologically acceptable salts thereof;
wherein $R^1$ to $R^9$ are defined above. General procedures for making compounds which are useful in this invention are well known in the art and have been described, for example, in the following references: Scherrer, Robert A. et al. J. Org. Chem. 45, 2127, 1980; Wassamundt, Frederick W. et al. J. Org. Chem. 60, 1713, 1995; Zabrowski, Daniel, L. et al. Tetrahedron Lett. 29, 4501, 1988; Edwards, R. L. et al. J. Chem. Soc. 4084, 1964.

It has now been discovered that the novel compounds of this invention possess immunosuppressive activity as confirmed through a drug screen. Specific T cell proliferation was measured in response to antigen exposure in the presence or absence of novel compounds. It was found that novel compounds inhibited T cell proliferation by 50% ($IC_{50}$) at a concentration of about 10 to 100 nM. This compares favorably with cyclosporin A, which has an $IC_{50}$ at 15 nM (Table).

One embodiment of the present invention is a method of suppressing T cell mediated immune responses. The T cell mediated immune responses can be in an individual (i.e., a human) or animal. Suitable animals include farm animals (e.g., cows, pigs, sheep, goats and the like) and veterinary animals (e.g., dogs, cats, guinea pigs, horses and the like). The T cell mediated immune response can also be in vitro.

As used herein, a "T cell mediated immune response" refers to the increased proliferation of T cells in response to antigen compared with the proliferation of T cells in the absence of antigen. A "T cell mediated immune response" also refers to the increased release by T cells of factors such as cytokines in response to antigen. Examples of cytokines released from T cells in response to antigen include interleukin (IL-2) and interleukin 4 (IL-4). The methods of treatment disclosed herein are useful for treating autoimmune disorders in which there is a T cell mediated immune response to a self antigen. A "self-antigen" includes a molecule, peptide, protein, nucleic acid, carbohydrate, cell or combination thereof produced by an individual or animal which causes a T cell mediated immune response in the individual or animal.

"Suppressing" a T cell mediated immune response refers to decreasing or slowing the proliferation of T cells in response to antigen. Alternatively, "suppressing" a T cell mediated immune response refers to decreasing or slowing the release of factors from T cells in response to antigen. In an individual or animal, the suppression of a T cell mediated immune response can also refer to increasing the life span or ameliorating the symptoms of an individual or animal having an autoimmune disease such as insulin dependent diabetes mellitus, ulcerative colitis, rheumatoid arthritis, multiple sclerosis and lupus erythematosus. Examples of symptoms which can be ameliorated include hyperglycemia in diabetes, joint pain, stiffness and immobility in rheumatoid arthritis, paralysis in multiple sclerosis and rash and skin lesion in lupus erythematosus. With respect to insulin dependent diabetes mellitus, suppressing a T cell mediated immune response also refers to administering the compound before secondary complications resulting from the disease arise, such as vascular disorders.

Another embodiment of the present invention is a method of suppressing organ transplant rejection in an individual or animal who has received an organ transplant. An "organ transplant" refers to transferring or "transplanting" an internal organ (e.g. heart, lung, kidney, liver, pancreas, stomach, large intestine and small intestine) or external organ (e.g. skin) from a donor to a recipient, wherein the donor is genetically distinct from the individual or animal who has received the transplant. An "organ transplant" also includes cross species transplants.

"Suppressing organ transplant rejection" refers to increasing the period of time in which a transplanted organ can function in a recipient's body without undergoing rejection. Alternatively, "suppressing organ transplant rejection" includes reducing the severity or intensity of a T cell mediated immune response to a transplanted organ in a recipient. "Suppressing organ transplant rejection" also includes treating graft versus host disease, wherein the immune response of the graft cells is activated by antigen produced by the transplant recipient. In this instance, "suppressing organ transplant rejection" refers to suppressing the immune response of the graft cells.

"A therapeutically effective amount" is the dosage of compound required to achieve the desired therapeutic and/or prophylactic effect, for example the dosage of the compound which results in suppression of an immune response in the individual or animal, or which results in suppression of an organ transplant rejection in the individual or animal.

The specific dosage level of active ingredient will depend upon a number of factors, including biological activity of the novel compounds, age, body weight, sex, general health, severity of the particular disease to be treated and the degree of immune suppression desired, as well as appropriate pharmacokinetic properties. For example, dosages can be from about 10 mg/kg/day to about 1000 mg/kg/day. An effective amount of the compound can be administered by an appropriate route in a single dose or multiple doses.

A variety of routes of administration are possible including, but not necessarily limited to parenteral (e.g., intravenous, intraarterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's pharmaceutical Science*, 16th Edition, Mack, Ed. (1980)).

An "inhibitory amount" of the compound is the amount which, when contacted with T cells in vitro, results in decreased proliferation of the T cells or decreased release of factors from the T cells in response to antigen compared with in the absence of the compound. An inhibitory amount is typically about 1 μM to about 0.1 nM, preferably about 100 nM to about 1 nM.

In one embodiment, novel compounds can be applied topically as a cream or ointment to locally deliver immunosuppressive concentrations of the drug without significant systemic exposure. Topical application may be the ideal way to deliver the compound in psoriasis and perhaps other inflammatory skin diseases such as contact dermatitis and pemphiqus vulgaris.

Counterions which result in physiologically acceptable salts of the compounds, including protonated salts thereof, are within the scope of this invention and include but are not limited to salts derived from inorganic cations such as sodium (Na$^+$), potassium (K$^+$), lithium (Li$^+$), and the like; organic bases such as mono-, di- and trialkyl amines of 1–8 carbon atoms, per alkyl group and mono-, di- and trihydroxyalkyl amines of 1–8 carbon atoms peralkyl group, and the like; and organic and inorganic acids such as acetate, lactate, citrate, tartrate, succinate, maleate, malonate, gluconate, hydrochloride, hydrobromide, phosphorate, nitrate, sulfate, trifluoromethansulfonate, methanesulfonate, and similarly known acceptable acids.

The compound can be administered alone or in conjunction with other pharmacologically active agents, e.g., together with other immunosuppressive agents or together with antibiotics and/or antiviral agents. Compounds that can be coadministered include steroids (e.g. methyl prednisolone acetate), NSAIDS and other known immunosuppressants such as azathioprine, 15-deoxyspergualin, cyclosporin, mizoribine, mycophenolate mofetil, brequinar sodium, leflunomide, FK-506, rapamycin and related molecules. Dosages of these drugs will also vary depending upon the condition and individual to be treated.

The assay used to measure T cell growth inhibition was a human peripheral blood lymphocyte (PBL) proliferation assay using standard procedures known in the art. PBL's were chosen due to their known ability to proliferate in the presence of antigens derived from herpes simplex virus (HSV), Rubella or tetanus toxoid (TT). PBL growth inhibition was measured in terms of the compounds' ability to interfere with antigen induced lymphocyte proliferation.

The novel compounds can be used to produce antibodies (e.g., polyclonal and monoclonal) against the complexes. Methods for making antibodies are well known. The antibodies can be used as a diagnostic tool for monitoring the amount of immunosuppressant compound in patient blood levels. The ability to closely monitor the amount of the novel compound provides a suitable means for controlling drug delivery to patients in both preclinical and clinical settings.

It is known that compounds having T lymphocyte immunosuppressive properties may also be useful in inhibiting the proliferation of cardiac smooth muscle cells. Based upon this, it is expected that the compounds can be used for the treatment of hyperproliferative vascular disorders, such as restenosis and atherosclerosis.

The invention also provides a method for coadministration of the compounds described herein with agents designed for gene therapy. It is believed that the use of the compounds of this invention may suppress the immune system and reduce/minimize an immune response against the gene delivery vehicle, so that therapeutic levels of transgene expression can be achieved in an animal or human. Any type of gene therapy delivery vehicle can be coadministered, such as those well known in the art. Concurrent administration of the gene therapy delivery vehicle and the compounds of this invention, either as a single unit dose or taken individually, is preferred.

The invention will be further illustrated by the following non-limiting Examples:

EXAMPLE 1

Preparation of PRO 3249

To a 300 mL isopropyl alcohol solution of 5.97 g (0.0245 mol) 3,3'-dimethoxybenzidine and 0.148 g (0.00005 mol) Cu(OAc)2 was added a 100mL isopropyl alcohol solution of 5.86 g (0.0163 mol) diphenyliodonium-2-carboxylate dropwise over 1 hour at 100° C. The reaction mixture was refluxed for 2 hours and was monitored by analytical HPLC. The reaction mixture was cooled to room temperature, filtered through celite and the solvent was removed under reduced pressure.. The product was purified by flash chromatography utilizing three successive columns: 1) 76% CHCL$_3$, 20% MeOH, 4% NH$_4$OH; 2) 0.1% TFA (trifluoroacetic acid) ethyl acetate; 3) 76% CHCL$_3$, 20% MeOH, 4% NH$_4$OH. The product was titrated with a solution of 0.25M NaOH/MeOH (⅓ vol/vol), the solution was stirred for 2 hours at room temperature and then the solvent was removed under reduced pressure to afford the sodium salt. $^1$H NMR (DMSO-d$_6$, 250 MHz) δ 7.77 (dd, 1H), 7.34 (d, 1H), 7.16 (m, 6H), 6.68 (d, 1H), 6.61 (dd, 1H), 4.75 (b, 2H), 3.85 (s, 3H), 3.84 (s, 3H); Negative FAB MS [M-H]$^-$ 360.

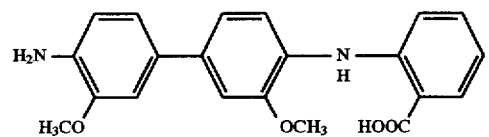

EXAMPLE 2

Preparation of PRO 4323

To a mixture of 0.363 g (1 mmol) PRO 3249 in 10 mL dioxane and 0.150 g (1.5 mmol) KHCO$_3$ in 2 mL H$_2$O was added 0.327 g (1.5 mmol) di-tert-butyl dicarbonate at room temperature. The reaction was stirred overnight at room temperature and then acidified with 10% HCl to pH ˜3. To the reaction mixture was added 20 mL ethyl acetate, the organic phase was separated from the aqueous phase and removed under reduced pressure. PRO 4323 was purified by flash chromatography with a straight gradient of 70% hexane, 30% ethyl acetate and 0.5% HOAc to yield 0.08 g pure PRO 4323. $^1$H NMR (DMSO-d$_6$, 250MHz) δ 9.67 (s, 1H), 7.95 (s, 1H), 7.91 (d, 1H), 7.76 (d, 1H), 7.45 (m, 6H), 6.77 (dd, 1H), 3.92 (s, 3H), 3.90 (s, 3H), 1.46 (s, 9H); Negative FAB MS [M-N]$^-$ 463.

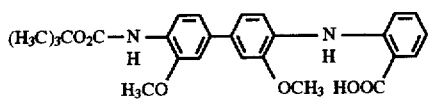

EXAMPLE 3

PRO 4379

To a solution of 0.100 g (0.275 mmol) PRO 3249 and 0.0334 g (0.330 mmol) Et$_3$ in tetrahydrofuran (THF) (10 mL) was added 0.0259 g (0.330 mmol) acetyl chloride in 2 mL THF dropwise under argon. The reaction was monitored by reverse phase analytical HPLC. After the reaction was stirred for 3 hours at room temperature, the solvent was removed under reduced pressure. PRO 4379 was purified by reverse phase preparative HPLC. $^1$H NMR (DMSO-d$_6$, 250 MHz) δ 9.66 (s, 1H), 9.19 (s, 1H), 8.02 (d, 2H), 7.91 (d, 2H), 7.46 (m, 7H), 6.80 (dd, 1H), 3.92 (s, 6H), 2.09 (s, 3H); Negative FAB MS [M-H]$^-$ 406.

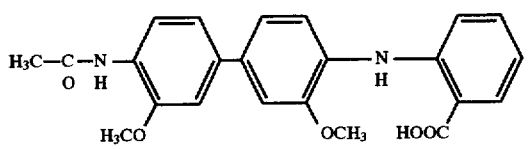

EXAMPLE 4

PRO 5023

To a solution of 0.080 g (0.263 mmol) PRO 4707 and 0.080 g (0.789 mmol) Et$_3$N in 4 mL of THF was added 0.0619 g (0.789 mmol) acetyl chloride in 1 mL THF under argon. The reaction was monitored by reverse phase analytical HPLC. After the solution was stirred at room temperature for 3 days, the solvent was removed under reduced pressure. PRO 5023 was purified by reverse phase preparative HPLC. $^1$HNMR (DMSO-d$_6$, 250 MHz) δ 10.01 (s, 1H), 9.68 (s, 1H), 7.91 (d, 1H), 7.63 (m, 10H), 6.79 (dd 1H), 2.05 (s, 1H); Negative FAB MS [M-H]$^-$ 345.

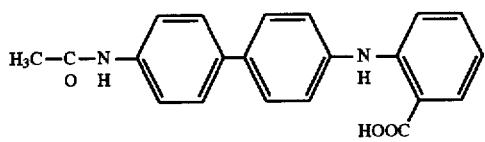

EXAMPLE 5

PRO 4402

To a suspension of 0.0693 g (1.1mmol) NaNO$_2$ in 2 g of crushed ice was added a 30 mL solution of MeOH/H$_2$O (8:2) of 0.363 g (1mmol) PRO 3249 and excess HBr (48%) over 2 hours at 0°–5° C. (ice bath). The reaction solution was stirred one hour at room temperature. Without separation, the diazonium salt of PRO 3249 was added to a solution of 0.172 g (1.2 mmol) CuBr and excess HBr (48%) at 90° C. The reaction progression was monitored by analytical HPLC. After the solution was stirred for 1 hour at 90°–100° C., the reaction mixture was cooled to room temperature. The solvent was removed under reduced pressure and the product was purified by flash chromatography with a straight gradient (10% Et$_2$O, 90% hexane, 0.5% HOAc). $^1$H NMR (DMSO-d$_6$, 250 MHz) δ 9.73 (s, 1H), 7.91 (dd, 1H), 7.62 (d, 1H), 7.49 (m, 7H), 6.82 (dd, 1H), 3.95 (s, 3H), 3.93 (s, 3H); Negative FAB MS [M-H]$^-$ 428.

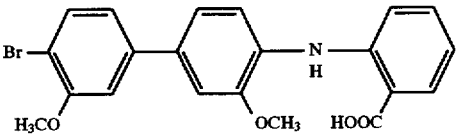

EXAMPLE 6

PRO 4403

To 0.33 mL 40% HBF$_4$ (2.5 mmol) diluted with 0.4 mL H$_2$O was added a 20 mL H$_2$O solution of 0.381 g (1 mmol) PRO 3249 at 0°–5° C.; the resulting very fine suspension was stirred for 30 min at 0°–5° C. To the fine suspension was added 0.0828 g (1.2 mmol) NaNO$_2$ dissolved in 2 mL H$_2$O. The reaction mixture was stirred for 1 hour at 0°–5° C. A thick precipitate was formed and was filtered. The residue was dried at high vacuum overnight. A 20 mL dimethylformamide (DMF) solution of the residue was added to a 10 mL DMF suspension of 0.278 g (1 mmol) FeSO$_4$ 7H$_2$O dropwise at room temperature. The reaction mixture was stirred for 2 hours at room temperature (until all the diazonium salt was converted to PRO 4403 as shown by analytical HPLC). To the reaction mixture was added water and ethyl acetate (EtOAc), the organic layer was removed in vacuo and the product was purified by flash chromatography with a straight gradient of 76% CHCl$_3$, 20% MeOH, 4% NH$_4$OH. The fraction was dried under reduced pressure and titrated with a solution of 0.25M NaOH/MeOH (½ ratio vol/vol) and, the solution was stirred for 2 hours at room temperature. The solvent was removed under reduced pressure to afford the sodium salt. $^1$H NMR (DMSO-d$_6$, 250 MHz), δ 9.69 (s, 1H), 7.91 (dd, 1H), 7.47 (m, 8H), 6.89 (dd, 1H), 6.79 (dd, 1H), 3.92 (s, 3H), 3.81 (s, 3H); Negative FAB MS [M-H]$^-$ 348.

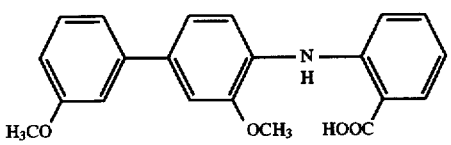

EXAMPLE 7

PRO 4636

To a solution of 1.089 g (3 mmol) PRO 3249 in 200 mL acetone, 30 mL CH$_2$Cl$_2$ was added 15 mL 0.8M Na$_3$PO$_4$ and 0.051 g (0.15 mmol) tetrabutylammonium hydrogen sulfate. To the chilled (0°–5° C.) suspension was added 30mL 2N KOH and 45 mL of an aqueous solution of 6 g (9.6 mmol) oxone at the same time by dropwise addition over 40 minutes. The reaction solution was stirred for one more hour at 0°–5° C. The excess oxidation reagent was quenched with 0.2 mL methyl sulfide. The reaction solution was acidified with 10% HCl to pH ~4, 200 mL CH$_2$Cl$_2$ was added, the organic phase was separated from the aqueous phase and was concentrated under reduced pressure. The crude product was purified by flash chromatography to yield 0.2 g PRO 4636 which was repurified by reverse phase HPLC. $^1$HNMR (DMSO-d$_6$, 250 MHz) δ 9.8 (s, 1H), 7.94 (dd, 2H), 7.54 (m, 7H), 6.85 (dd, 1H), 4.03 (s, 3H), 3.95 (s, 3H); Negative FAB MS [M-H]$^-$ 393.

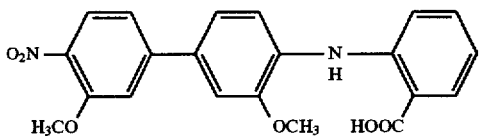

EXAMPLE 8

PRO 5021

To a solution of 0.100 g (0.275 mmol) PRO 3249 in anhydrous MeOH (10 mn) was added 0.1mL (excess) 4N HCl in dioxane. The reaction mixture was monitored by TLC. After 16 hours at reflux, the reaction was cooled to room temperature. The solvent was removed under reduced pressure. The PRO 5021 was purified by flash chromatography with a straight gradient (40% EtOAc / 60% Hexane / 0.1% Et$_3$N) to afford 50 mg PRO 5021. $^1$HNMR (DMSO-d$_6$, 250MHz) δ 9.38 (s, 1H), 7.90 (dd, 1H), 7.41 (m, 2H), 7.24 (m, 5H), 6.80 (dd, 1H), 6.70 (d, 1H), 4.83 (s, 2H), 3.90 (s, 3H), 3.85 (s, 3H), 3.32 (s, 3H); Positive FAB MS [M+H]$^+$ 379.

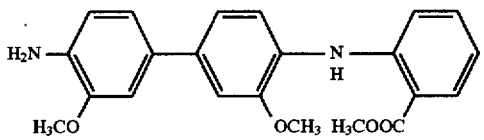

EXAMPLE 9

Preparation of PRO 4707, 4708, 4916, 4918, 4919

An isopropyl alcohol solution of benzidine derivative and diphenyl iodonium-2-carboxylate in a 1.3 to 1 ratio with a catalytic amount (0.5%) of Cu(OAc)$_2$ was refluxed for 2–4 hours. The reactions were monitored by reverse phase analytical HPLC. The products were purified by reverse phase preparative HPLC.

PRO 4707: $^1$H NMR (DMSO-d$_6$, 250 MHz) δ 9.68 (s, 1H), 7.91 (dd, 1H), 7.59 (m, 8H), 6.98 (d, 2H), 6.77(dd, 1H); Negative FAB MS [M-H]$^-$ 303.

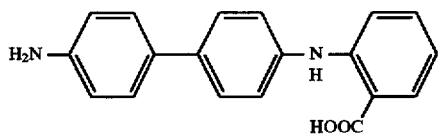

PRO 4708: $^1$H NMR (DMSO-d$_6$, 250 MHz) δ 9.81 (s, 1H), 7.95 (d, H), 7.49 (m, 8H), 6.93 (m, 1H) 6.60 (d, 2H); Negative FAB MS [M-H]$^-$ 331.

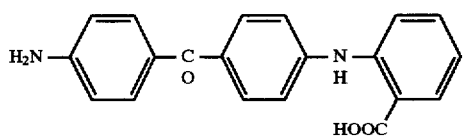

PRO 4916: $^1$H NMR (DMSO-d$_6$, 250 MHz) δ 9.65 (s, 1H), 7.91 (dd, 1H), 7.56 (d, 2H), 7.45 (m, 2H), 7.21 (m, 3H), 7.09 (d, H), 6.77 (dd, 1H), 3.91 (s, 3H); Negative FAB MS [M-H]$^-$ 333.

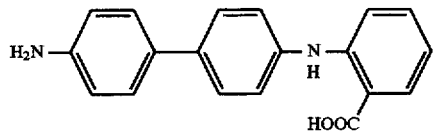

PRO 4918: $^1$H NMR (DMSO-d$_6$, 250 MHz) δ 9.53 (s, 1H), 9.90 (dd, 1H), 7.55 (d, 1H), 7.46 (m, 5H), 7.04 (d, 1H), 6.96 (d, H), 6.74 (dd, 1H), 2.25 (s, 6H); Negative FAB MS [M-H]$^-$ 331.

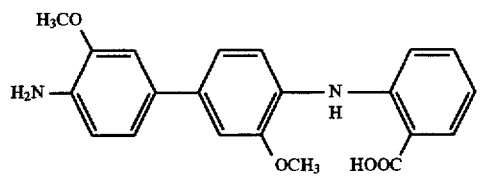

PRO 4919: $^1$H NMR (DMSO-d$_6$, 250 MHz) δ 9.69 (s, 1H), 7.92 (dd, 1H), 7.50 (m, 4H), 7.17 (dd, 1H), 6.96 (d, 1H), 6.83 (dd, 3H); Negative FAB MS [M-H]$^-$ 331.

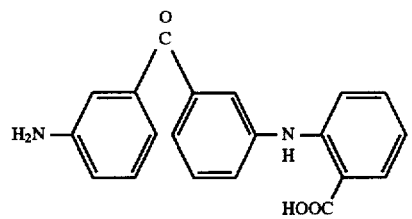

EXAMPLE 10

Preparation of PRO 4917

An isopropyl alcohol solution of aniline derivative and diphenyliodonium-2-carboxylate in a 1 to 1 ratio with a catalytic amount (0.5%) Cu (OAc)$_2$ was refluxed for 2–4 hours. The reactions were monitored by reverse phase analytical HPLC. The product from the reaction was purified by reverse phase preparative HPLC or flash chromatography.

PRO 4917: $^1$H NMR (DMSO-d$_6$, 250 MHz) δ 9.70 (s, 1H), 7.92 (dd, 1H), 7.66 (d, 4H), 7.41 (m, 7H), 6.83 (dd, 1H); Negative FAB MS [M-H]$^-$ 288.

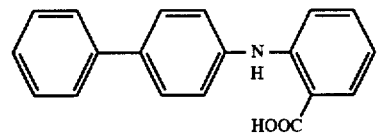

EXAMPLE 11

PRO 5106

A solution of 0.200 g (0.50 mmol) PRO 4636 in thionyl chloride (10 mL) was refluxed for 1 hour. The reaction mixture was cooled to room temperature and the solvent was removed under reduced pressure. To a solution of the residue (crude product - acid chloride ) in 5 mL THF was added 1 mL2.0M NH$_3$/MeOH at room temperature. The reaction was monitored by TLC. After the solution was stirred for 1 hour at room temperature, the solvent was removed under reduced pressure. The product (100 mg free amide) was purified by reverse phase chromatography.

A 2 mL phosphorous oxychloride solution of 0.100 g (0.254 mmol) free amide was stirred for 10 minutes at room temperature. Ice was added to quench excess phosphorous oxychloride, the product was extracted with CHCl₃ and the solvent was removed under reduced pressure.

To a solution of 0.078 g (0.208 mmol) the resultant product in 5 mL DMF was added 0.11 g (2.08 mmol) NH₄Cl and 0.135 g (2.08 mmol) NaN₃. The reaction solution was heated to 120° C. for 2 days while being monitored by reverse phase analytical HPLC. Product PRO 5106 was purified by reverse phase preparative HPLC. ¹H NMR (DMSO-d₆, 250 MHz) δ 9.49 (s, 1H), 7.98 (d, 1H), 7.96 (dd, 1H), 7.54 (m, 8H), 4.04 (s, 3H), 4.01 (s, 3H); Negative FAB MS [M-H]⁻ 417.

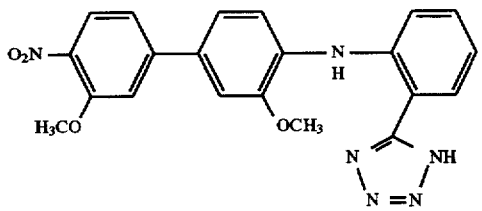

EXAMPLE 12

PRO 5105

To a suspension of 0.030 g (0.0735mmol) PRO 5106 in 16 mL EtOH/H₂O (15/1) was added 0.1 g Pd/C (10%) and 0.20 g NaBH₄. The reaction mixture was stirred for 10 minutes at room temperature and was monitored by reverse phase analytical MPLC. The reaction mixture was filtered through celite and the solvent was removed under reduced pressure to afford PRO 5105 (amino-tetrazole) which was purified by reverse phase preparative HPLC. ¹H NMR (DMSO-d₆, 250 MHz) δ 9.49 (s, 1H), 7.98 (d, 1H), 7.96 (dd, 1H), 7.54 (m, 8H), 4.04 (s, 3H), 4.01 (s, 3H); Negative FAB MS [M-M]⁻ 387.

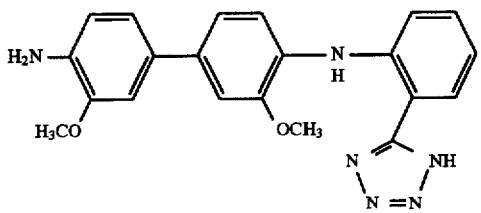

EXAMPLE 13

PRO 6365 and PRO 6370

To a mixture of 0.1 g (0.275 mmol) PRO 3249 and 0.1 g (0.7mmol) methyl iodide in anhydrous acetonitrile was added powdered potassium carbonate (0.073 g, 0.53 mmol). The reaction mixture was refluxed for three hours. 10 mL ethyl acetate was added and the organic phase was washed with water and evaporated under reduced pressure. Reverse phase preparative HPLC yielded both the monomethyl amine and the dimethyl amine methyl esters of PRO 3249.

The dimethyl amine methyl ester of PRO 3249 (0.1 g, 0.255 mmol) was treated with a 2M NaOH/MeOH solution (20 ml). The resulting acid was purified by flash chromatography (76 % CHCl₃, 20 % MeOH, 4 % NH₄OH) and the product was titrated with a solution of 0.25M NaOH/MeOH in a ⅓ (v/v) ratio to give PRO 6365. Negative FAB MS [M-H]⁻ 391.

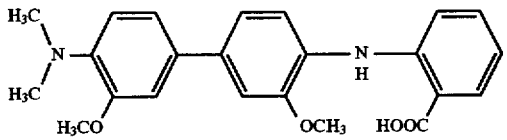

EXAMPLE 14

PRO 6370

The monomethyl amine methyl ester of PRO 3249 (0.07 g, 0.179 mmol) was treated with a 2M NaOH/MeOH solution (20 mL). The resulting acid was first purified by flash chromatography (76 % CHCl₃, 20 % MeOH, 4% NH₄OH) followed by purification by reverse phase preparative HPLC. The product was titrated with a solution of 0.25M NaOH/MeOH in a ⅓ (v/v) ratio to give PRO 6370. Negative FAB MS [M-H]⁻ 377.

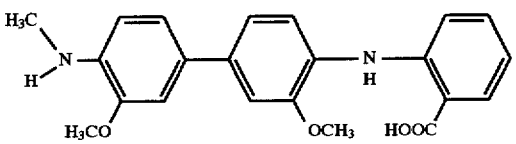

EXAMPLE 15

PBL Antigen Specific Proliferation Assay

The lymphocytes were prepared by first separating them from the blood samples of several donors by Ficoll gradient separation as described by standard procedure known in the art. The isolated lymphocytes were then grown in RPMI 1640 medium containing 5% human AB serum, glutamine (2 mM), penicillin/streptomycin, 50 μ/ml/50 μg/ml sodium pyruvate (1 mM) and HEPES buffer (10 mM).

For assay purposes, PBL's were incubated at a density of 10⁵ per 200 μl of medium per well of a 96-well plate. Tetanus toxoid (TT; Connaught Labs, Willow Dale, ON) was used as a stimulating antigen at a concentration of 5 LF/ml.

The test wells containing PBL's, were exposed to tetanus toxoid antigen, along with various dilutions of the novel compounds solutions, as shown in the Table.

Subsequently, TT antigen/novel compounds exposed PBL's were pulsed with 1 μCi/well of ³H-thymidine on day 5 using a standard procedure known in the art. The cells were then harvested 16 hours later onto a glass fiber filter using a TOMTEC cell harvester. Thymidine incorporation was measured by liquid scintillation counting using a Beta plate counter (Pharmacia, Inc., Piscataway, N.J.).

The results of the assay are shown in the Table.

EXAMPLE 16

Mixed Lymphocyte Reactions (MLR) Assay

Blood samples were drawn from two donors and the lymphocytes were separated out by Ficoll gradient by standard procedures known in the art. The isolated lymphocytes from done 1 were left untreated and the cells from donor 2 where suspended in Hanks Balanced Salt Solution at $10^7$/ml and treated with 50 micrograms/ml mitomycin C for 30 minutes at 37° C.

The PBLs were cultured in RPMI 1640 medium containing 5% human AB serum, glutamine (2 mM), penicillin/ streptomycin (50 micrograms/ml / 50 micrograms/ml), sodium pyruvate (1 mM) and HEPES buffer (10 mM). For assay purposes, $10^5$ PBLs from each donor were added to each well of a 96-well plate in a total volume of 200 microliters along with various dilutions of test compound.

The cultures were pulsed with 1 microCurie $^3$H-thymidine on day 5 and harvested 16 hours later onto a glass fiber filter. Thymidine incorporation was measured by liquid scintillation counting using a Beta plate counter. The $IC_{50}$ represents the amount of compound necessary to inhibit 50 % of the thymidine incorporation.

TABLE

| PRO # | $IC_{50}$ (ng/mL) |
|---|---|
| PRO3249 | 5 |
| PRO4323 | 15 |
| PRO4379 | 133 |
| PRO4402 | 30 |
| PRO4403 | 12 |
| PRO4636 | 3200, H9 assay |
| PRO4707 | 86 |
| PRO4708 | 345 |
| PRO4916 | 29 |
| PRO4917 | 296 |
| PRO4918 | 73 |
| PRO4919 | 5000, MLR assay |
| PRO5021 | 37 |
| PRO5023 | >1000 |
| PRO5105 | >1000 |
| PRO5106 | >1000 |
| PRO6365 | 194 |
| PRO6370 | 10 |

EXAMPLE 17

H9 proliferation Assay

The human transformed T cell line, H9 (ATCC Rockville, Md.), was cultured at 3000/well in RPMI 1640 medium supplemented with 5 % human AB serum, glutamine (2 mM), penicillin/streptomycin (50 U/ml, 50 micrograms/ml), sodium pyruvate (1 mM), HEPES (10 mM), and nonessential amino acids (1X) in a total of 200 microliter/well in a 96 well plate. The H9 cells were cultured with and without various dilutions of test compound for 3 days.

The cells were pulsed on day 3 with 1 microCurie/well of $^3$H-thymidine using a standard procedure known in the art. The cells were then harvested 16 hours later onto glass fiber filters using a TOMTEC cell harvester. Cellular proliferation was assessed by thymidine incorporation and measured by liquid scintillation counting using a Beta plate counter (Pharmacia, Inc., Piscataway, N.J.). The IC 50 represents the amount of compound necessary to inhibit 50% of the thymidine incorporation.

Equivalents

Those skilled in the art will recognize, or be able to ascertain, using no more than routine experimentation many equivalents to the specific embodiments of the invention described herein. Such equivalents are intended to be encompassed by the following claims:

We claim:
1. A compound having the formula:

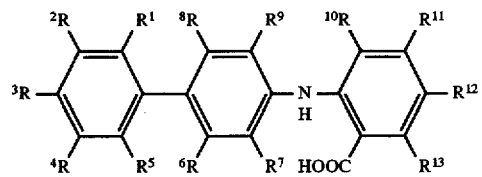

and physiologically acceptable salts thereof;

wherein $R^1$ to $R^{13}$ are independently selected from the group consisting of $C_2$–$C_4$ linear and branched alkyls, H, $NH_2$, $CH_3$, $OR^{14}$, fluorine, chlorine, bromine, iodine, $NO_2$, $CF_3$, $NHCOCH_3$, $NHCOOtBu$, $NHR^{15}$, $NR^{16}R^{17}$ and phenyl, wherein $R^{14}$ is a $C_1$–$C_8$ linear or branched alkyl;

wherein $R^{15}$ is selected from the group consisting of $C_2$–$C_4$ linear and branched alkyls;

wherein $R^{16}$ and $R^{17}$ are independently selected from the group consisting of H and $C_2$–$C_4$ linear and branched alkyls.

2. The compound of claim 1 wherein the compound is represented by a structural formula selected from:

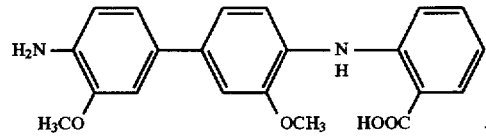

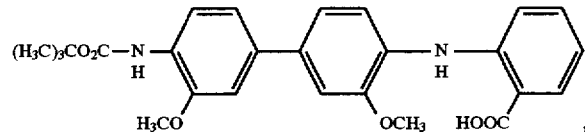

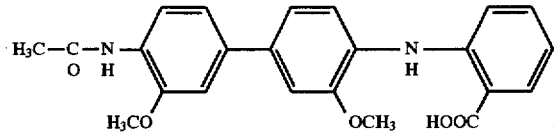

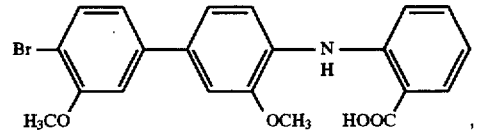

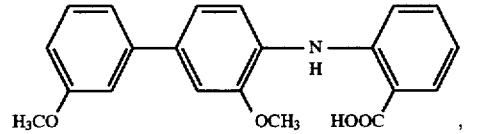

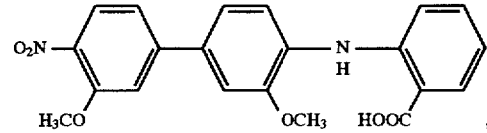

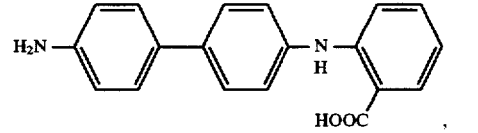

-continued

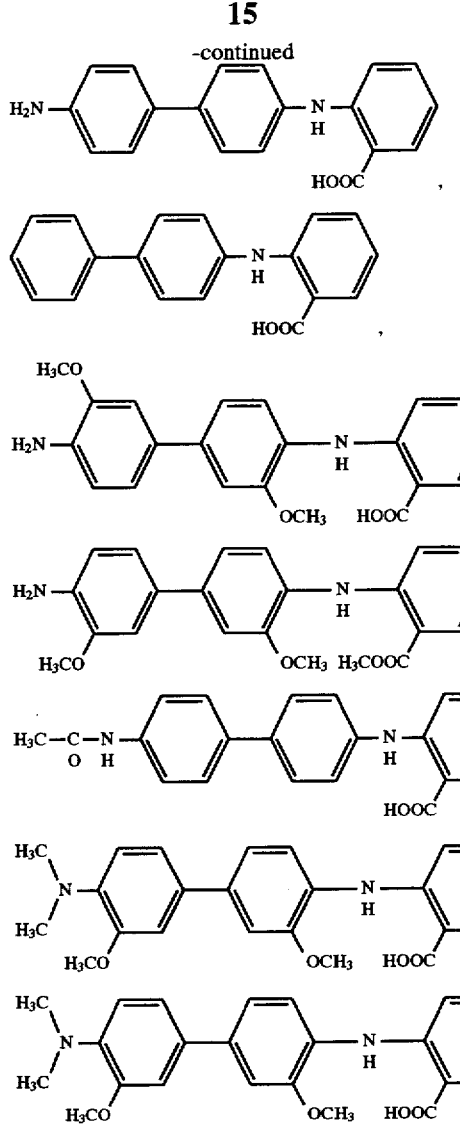

3. A composition comprising a physiologically acceptable vehicle and an immunosuppressive amount or an antiproliferative amount of a compound having the general formula:

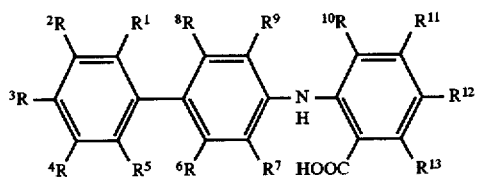

and physiologically acceptable salts thereof;
  wherein $R^1$ to $R^{13}$ are independently selected from the group consisting of $C_2$–$C_4$ linear and branched alkyls, H, $NH_2$, $CH_3$, $OR^{14}$, fluorine, chlorine, bromine, iodine, $NO_2$, $CF_3$, $OR^{14}$, $NHCOCH_3$, $NHCOOtBu$, $NHR^{15}$, $NR^{16}R^{17}$ and phenyl, wherein $R^{14}$ is a $C_1$–$C_8$ linear or branched alkyl;
  wherein $R^{15}$ is selected from the group consisting of $C_2$–$C_4$ linear and branched alkyls;
  wherein $R^{16}$ and $R^{17}$ are independently selected from the group consisting of H and $C_2$–$C_4$ linear and branched alkyls.

4. The composition of claim 3 wherein the compound is represented by a structural formula selected from:

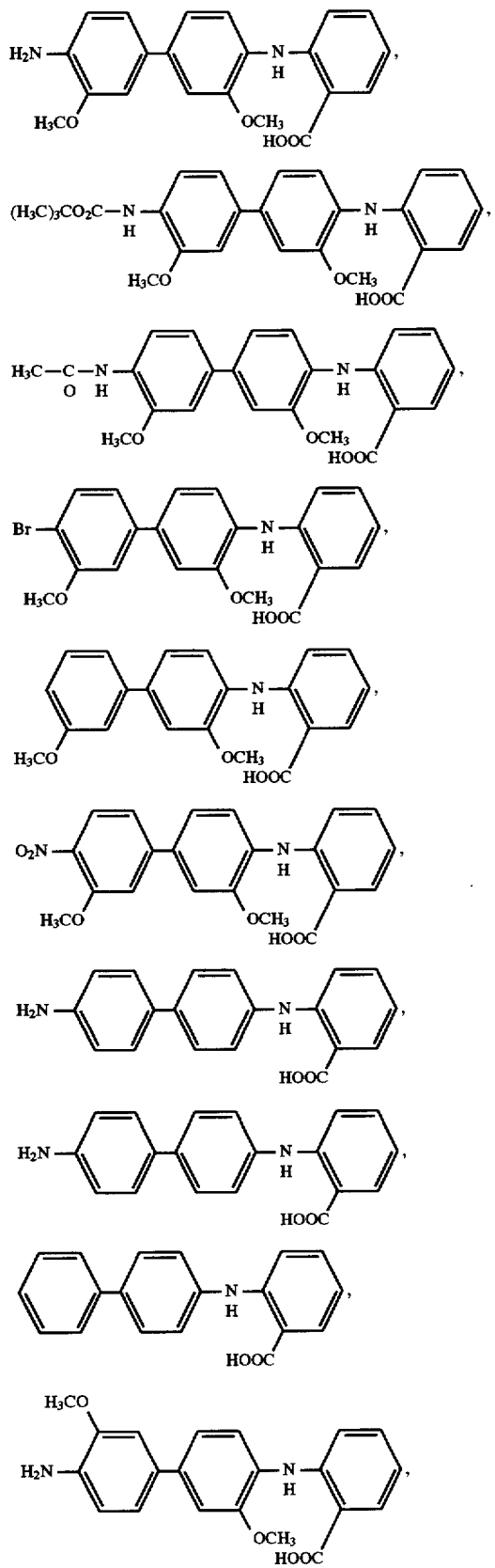

-continued

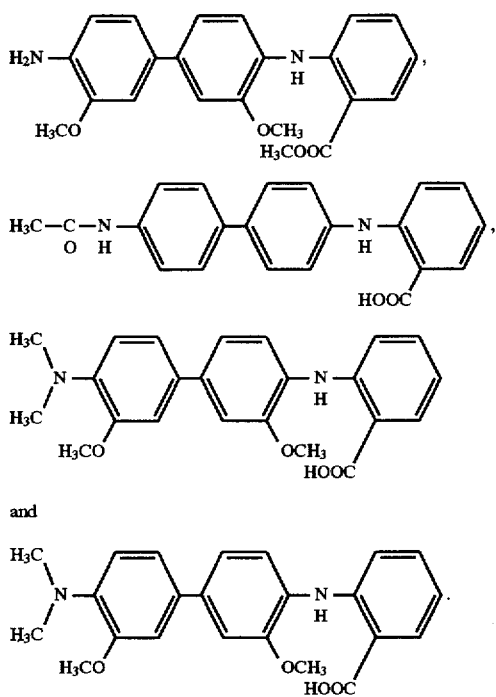

and

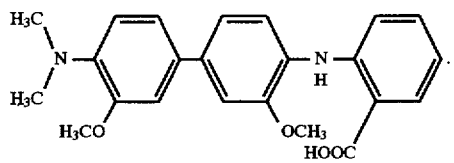

5. A method of preventing or substantially reducing a T-lymphocyte mediated immune response of a mammal comprising administering to a mammal, a compound having the general formula:

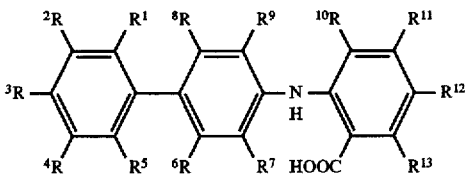

and physiologically acceptable salts thereof;

wherein $R^1$ to $R^{13}$ are independently selected from the group consisting of $C_2$–$C_4$ linear and branched alkyls, H, $NH_2$, $CH_3$, $OR^{14}$, fluorine, chlorine, bromine, iodine, $NO_2$, $CF_3$, $NHCOCH_3$, $NHCOOtBu$, $NHR^{15}$, $NR^{16}R^{17}$ and phenyl, wherein $R^{14}$ is a $C_1$–$C_8$ linear or branched alkyl;

wherein $R^{15}$ is selected from the group consisting of $C_2$–$C_4$ linear and branched alkyls;

wherein $R^{16}$ and $R^{17}$ are independently selected from the group consisting of H and $C_2$–$C_4$ linear and branched alkyls.

* * * * *

UNITED STATES PATENT AND TRADEMARK OFFICE
CERTIFICATE OF CORRECTION

PATENT NO. : 5,739,169
DATED : April 14, 1998
INVENTOR(S) : Timothy D. Ocain, Huai Gao, Jeffrey L. Krieger and Theresa M. Sampo It is certified that error appears in the above-identified patent and that said Letters Patent is hereby corrected as shown below:

In Claim 3, column 15, line 60, delete "$OR^{14}$".

In Claim 3, column 15, line 64, after "alkyls;" insert ---and---.

In Claim 5, column 18, line 24, after "alkyls;" insert ---and---.

Signed and Sealed this

Fourth Day of August, 1998

Attest:

BRUCE LEHMAN

*Attesting Officer*  *Commissioner of Patents and Trademarks*